United States Patent
Tortelli et al.

(10) Patent No.: US 9,051,259 B2
(45) Date of Patent: Jun. 9, 2015

(54) PROCESS FOR PRODUCING PERFLUORINATED ORGANIC COMPOUNDS

(75) Inventors: Vito Tortelli, Milan (IT); Marco Galimberti, Milan (IT)

(73) Assignee: SOLVAY SPECIALTY POLYMERS ITALY S.P.A., Bollate Milano (IT)

( * ) Notice: Subject to any disclaimer, the term of this patent is extended or adjusted under 35 U.S.C. 154(b) by 0 days.

(21) Appl. No.: 13/885,867

(22) PCT Filed: Nov. 17, 2011

(86) PCT No.: PCT/EP2011/070400
§ 371 (c)(1),
(2), (4) Date: May 16, 2013

(87) PCT Pub. No.: WO2012/069364
PCT Pub. Date: May 31, 2012

(65) Prior Publication Data
US 2013/0245289 A1    Sep. 19, 2013

(30) Foreign Application Priority Data
Nov. 22, 2010  (EP) .................................... 10192069

(51) Int. Cl.
| | |
|---|---|
| C07D 317/00 | (2006.01) |
| C07C 205/00 | (2006.01) |
| C07C 67/287 | (2006.01) |
| C07D 317/34 | (2006.01) |
| C07D 317/14 | (2006.01) |
| C07C 51/60 | (2006.01) |
| C07C 67/14 | (2006.01) |
| C07D 317/42 | (2006.01) |
| C07C 51/58 | (2006.01) |

(52) U.S. Cl.
CPC ............ *C07C 67/287* (2013.01); *C07D 317/34* (2013.01); *C07D 317/14* (2013.01); *C07C 2101/14* (2013.01); *C07C 51/60* (2013.01); *C07C 67/14* (2013.01); *C07D 317/42* (2013.01); *C07C 51/58* (2013.01)

(58) Field of Classification Search
CPC . C07D 317/34; C07D 317/14; C07C 2101/08
USPC .................................. 549/449; 560/125, 226
See application file for complete search history.

(56) References Cited

U.S. PATENT DOCUMENTS

| | | |
|---|---|---|
| 3,900,372 A | 8/1975 | Childs et al. |
| 5,093,432 A | 3/1992 | Bierschenk et al. |
| 2003/0149309 A1 | 8/2003 | Okazoe et al. |
| 2003/0216595 A1 | 11/2003 | Okazoe et al. |
| 2005/0020855 A1 | 1/2005 | Okazoe et al. |
| 2006/0074260 A1 | 4/2006 | Kaneko et al. |

FOREIGN PATENT DOCUMENTS

| | | |
|---|---|---|
| EP | 1164122 A1 | 12/2001 |
| EP | 1352892 A1 | 10/2003 |
| WO | WO 0146093 A2 | 6/2001 |

OTHER PUBLICATIONS

Smith M.B., et al—"March's Advanced Organic Chemistry, Reactions, Mechanisms, and Structure", 2001, 5th Edition, Chapter 10, pp. 482-483, John Wiley and Sons, Inc.; 4 pgs.

Morizawa, Yoshitomi—"Fluorine Chemistry at Asahi Glass; Present and Future", 2007, Asahi Garasu Kenkyu Hokoku (Res. Reports Asahi Glass Co. Ltd.), vol. 57, pp. 91-95; Includes partial translation and abstract in English; 6 pgs.

*Primary Examiner* — Andrew D Kosar
*Assistant Examiner* — Raymond Covington

(57) ABSTRACT

A process for producing a perfluorinated functional compound comprises the steps of:
A) converting an at least partially hydrogenated alcohol into an at least partially hydrogenated ester compound; and
B) reacting said at least partially hydrogenated ester compound with fluorine in the presence of at least one (per) haloolefin comprising at least one carbon-carbon double bond and having at least one fluorine or chlorine atom on either one of the carbon atoms of said double bond, to obtain a perfluorinated ester compound.

11 Claims, No Drawings

US 9,051,259 B2

PROCESS FOR PRODUCING PERFLUORINATED ORGANIC COMPOUNDS

CROSS-REFERENCE TO RELATED APPLICATIONS

This application is a U.S. national stage entry under 35 U.S.C. 371 of International Application No. PCT/EP2011/070400 filed Nov. 17, 2011, which claims priority to European application No. EP10192069.2 filed on Nov. 22, 2010, the whole content of this application being incorporated herein by reference for all purposes.

TECHNICAL FIELD

The invention relates to a process for producing functionalized perfluorinated organic compounds from hydrogen-containing alcohols.

BACKGROUND ART

It is known that perfluorinated organic compounds having functional moieties are useful intermediates for manufacturing a variety of valuable chemical compounds, such as perfluoromonomers (e.g. perfluorovinylethers) and fluorosurfactants.

A convenient approach for the synthesis of functional perfluorinated compounds involves fluorination of hydrogen-containing alcohols, the hydroxyl moiety being possibly derivatized to yield the target functional moiety. However, hydrocarbons containing functional hydroxyl moieties are generally unstable under conditions of traditional fluorination processes, typically comprising a first step carried out at low temperature and high dilution, followed by a further step involving high temperatures and high concentrations of fluorine, as required in order to reach satisfactory yields of the perfluorinated compound. Under these conditions, it is generally known that compounds having hydroxyl groups decompose, with simultaneous release of HF and $COF_2$, and subsequent formation of corresponding non-functional perfluorocompound having one less carbon atom than the starting hydroxyl-containing compound.

In order to overcome this problem, EP 1164122 A (ASAHI GLASS CO LTD) 19 Dec. 2001 discloses a process for producing fluorinated compounds wherein a primary hydrogenated alcohol is first converted into the corresponding ester, generally a partially fluorinated ester, by reaction with an acyl fluoride, preferably a (per)fluorinated acyl fluoride, and then subjected to fluorination in liquid phase. The so-obtained perfluorinated ester can be then thermally cleaved or decomposed with suitable agents, to obtain a perfluorinated acyl fluoride corresponding to the starting hydrogenated alcohol.

Similarly, US 2003/0216595 (ASAHI GLASS CO LTD) 20 Nov. 2003 discloses a process for producing a fluorinated ester, wherein a primary or a secondary hydrogenated alcohol is converted into the corresponding ester by reaction with a (per)fluorinated acyl fluoride and then subjected to fluorination in liquid phase. The so-obtained perfluorinated ester can be thermally cleaved or decomposed with suitable agents, to obtain a perfluorinated acyl fluoride or ketone corresponding to the starting hydrogenated alcohol.

Fluorination of hydrogenated esters with molecular fluorine to obtain the corresponding perfluorinated compounds has been also previously disclosed. For instance, U.S. Pat. No. 5,093,432 (EXFLUOR RESEARCH CORPORATION) 3 Mar. 1992 discloses a process for the liquid phase fluorination of hydrogenated esters with fluorine in a perhalogenated liquid medium. The process is carried out under high diluted conditions. The use of trichloroethylene is mentioned as a cosolvent to improve the solubility of the hydrogenated starting material in the perhalogenated liquid medium.

However, the above described processes have the drawback that, in order to prevent decomposition of the reagents due to the reaction exothermicity, it may be necessary to operate under diluted conditions both of fluorine and of the hydrogen-containing starting material. Furthermore, to obtain a fully fluorinated product, a large excess of fluorine over the stoichiometrically required quantity, is needed. These conditions might negatively affect the reaction rate, yielding low productivity of the overall process.

Electrochemical fluorination of hydrogen-containing alcohols protected under the form of esters has also been disclosed. In particular, U.S. Pat. No. 3,900,372 (PHILLIPS PETROLEUM) 19 Aug. 1975 discloses a process for the production of perfluorinated organic compounds from hydrogen-containing alcohols. The process comprises protection of the hydroxyl moieties of the hydrogen-containing alcohol by reaction with a perfluorinated acyl fluoride, e.g. trifluoromethyl acyl fluoride, to yield the corresponding hydrogen-containing ester. Said ester is then subjected to an electrochemical fluorination step, and the resulting perfluorinated counterpart, still possessing the ester moiety, is subsequently cleaved by the action of fluoride ions to yield the corresponding perfluorinated acyl fluoride.

Nevertheless, electrochemical fluorination is a burdensome and energy-consuming procedure, which is generally less economically and industrially acceptable than fluorination with elemental fluorine, particularly when a single compound has to be obtained. Furthermore, yields in electrochemical fluorination are known to be mostly moderate or even poor, especially if high molecular weight compounds have to be fluorinated.

US 20060074260 A (KANEKO, Y. ET AL.) 6 Apr. 2006 discloses carrying out the fluorination process of a "substrate that cannot undergo a fluorination reaction independently" in the presence of a "substrate that rapidly undergoes a fluorination reaction independently". The "substrate that rapidly undergoes a fluorination reaction independently" is defined as a compound having at least one (but preferably more than one) site at which reaction with fluorine can proceed. Notable examples of said substrates include linear, branched or cyclic hydrocarbon compounds having 5 to 30 carbon atoms, which may contain a fluorine atom, an oxygen atom, or/and an unsaturated bond, provided at least one unsaturated bond or at least on C—H bond are present. The examples however show that the addition of hexane as a "substrate that rapidly undergoes a fluorination reaction independently" was not sufficient to promote the complete fluorination of the starting ester compound and that the addition of a second substrate, namely hexafluorobenzene, was required to obtain a fully fluorinated product. Additionally, the yield of the fully fluorinated product was only 35%.

There is thus still a need in the art for a process for producing perfluorinated compounds having a functional moiety from hydrogen-containing alcohols comprising a fluorination step that may be carried out under mild conditions and providing high yields.

DISCLOSURE OF INVENTION

It is thus an object of the present invention to provide a process for producing a perfluorinated compound comprising functional moieties from relatively inexpensive hydrogen-containing alcohols, which does not involve a burdensome electrochemical fluorination process and which advantageously evolves with high yields.

The process of the invention thus comprises:

A. converting an at least partially hydrogenated alcohol into a corresponding at least partially hydrogenated ester compound;

B. reacting said at least partially hydrogenated ester compound with fluorine in the presence of at least one (per)haloolefin comprising at least one carbon-carbon double bond and having at least one fluorine or chlorine atom on either one of the carbon atoms of said double bond, to obtain a perfluorinated ester compound.

In the present specification and in the claims the expression "at least partially hydrogenated" when referred to an alcohol or an ester is meant to indicate that said alcohol or said ester contains at least one C—H bond.

The presence of a (per)haloolefin in step B of the process, as above described, allows to carry out the process according to the invention under mild conditions, so that no undesired decomposition of the reagents occurs. Additionally, a very high conversion of the ester as well as a remarkable selectivity in the formation of the desired perfluorinated ester are obtained. Furthermore, to achieve full fluorination of all C—H bonds, a large excess of fluorine is not required, conversion of this latter being very high in the present process. Without intending to limit the invention to a particular theory, it is believed that the (per)haloolefin acts as radical initiator in the reaction of fluorine specifically with the ester and thus enables to achieve outstanding reaction rates in the fluorination step.

The expression "(per)haloolefin comprising at least one carbon-carbon double bond and having at least one fluorine or chlorine atom on either one of the carbon atoms of said double bond" is intended to encompass fluoroolefins, chloroolefins, and fluorochloroolefins, these compounds possibly comprising one or more heteroatom different from Cl and F, in particular oxygen. Preferably the (per)haloolefin is a perfluoroolefin.

According to an embodiment of the invention, the at least partially hydrogenated alcohol complies with formula $R_1R_2CHOH$ (I), wherein $R_1$ and $R_2$, independently of each other, are selected in the group consisting of: H, straight-chain, branched-chain and cyclic (oxy)hydrocarbon group, straight-chain, branched-chain and cyclic fluoro(oxy)hydrocarbon group.

In the present specification and in the claims, the term "(oxy)hydrocarbon group" is intended to indicate a hydrocarbon group or an oxyhydrocarbon group, said oxyhydrocarbon group comprising one or more than one catenary oxygen atoms. Similarly, the term "fluoro(oxy)hydrocarbon group" is intended to indicate a fluorohydrocarbon group or a fluorooxyhydrocarbon group, said fluorooxyhydrocarbon group comprising one or more than one catenary oxygen atoms. Other halogens, e.g. chlorine, might be possibly present in the at least partially hydrogenated alcohol of the invention.

$R_1$ and $R_2$ may, independently of each other, contain one or more hydroxyl group(s), so that the at least partially hydrogenated alcohol contains more than one hydroxyl group.

Preferably, said $R_1$ and $R_2$ groups, equal to or different from each other, are independently selected in the group consisting of H, $C_1$-$C_{20}$ (oxy)hydrocarbon group, $C_1$-$C_{20}$ fluoro(oxy)hydrocarbon group, $C_3$-$C_{20}$ cyclo(oxy)hydrocarbon group and $C_3$-$C_{20}$ fluorocyclo(oxy)hydrocarbon group.

According to one embodiment of the process, at least one of said $R_1$ and $R_2$ groups is H, so that said at least partially hydrogenated alcohol is a primary alcohol.

According to another embodiment, said alcohol is obtained in an optional, preliminary step of the process by ionic or radical addition of a hydrogenated alcohol to a perfluorinated or fluorinated olefin.

Said at least partially hydrogenated alcohol may be for example a $C_1$-$C_{18}$ monohydric or dihydric alcohol, preferably a $C_1$-$C_8$ aliphatic alcohol such as methanol, ethanol, 1-propanol, 1-butanol, 1,2-ethanediol, 1,3-propanediol.

The reactions and radical initiators that may be used to synthesize said at least partially hydrogenated, primary or secondary alcohol depend upon the specific desired compounds.

Non limiting examples of suitable perfluorinated or fluorinated olefins that may be used in said ionic or radical addition reaction are notably: $C_2$-$C_{18}$ fluoro and/or perfluoroolefins, preferably $C_2$-$C_{10}$ fluoro and/or perfluoroolefins, such as tetrafluoroethylene (TFE), hexafluoropropylene (HFP), pentafluoropropylene, octafluorobutene, hexafluorobutadiene; perfluoroalkylvinyl ethers, such as perfluoromethylvinylether, perfluoroethylvinylether, perfluoropropylvinylether; and fluorodioxoles, such as perfluorodioxole or perfluoromethoxydioxole.

In step A of the process, the at least partially hydrogenated alcohol is converted into an at least partially hydrogenated ester compound.

Standard methods for converting the at least partially hydrogenated alcohol into an at least partially hydrogenated ester can be used. Among others, suitable methods are notably described in SMITH, MICHAEL B., et al. March's Advanced Organic Chemistry, Chapter 10. 5th edition. John Wiley and Sons, 2001. p. 482-483. and references cited therein.

According to an embodiment of the process, said conversion may be achieved by reacting the alcohol with a reagent selected in the group consisting of acyl halides of formula $R_FC(O)X$ (IIa), wherein X=F, Cl, Br; preferably X=F.

Group $R_F$ in the acyl halide of formula (IIa) is typically selected in the group consisting of $C_1$-$C_{20}$ (oxy)hydrocarbon group, $C_1$-$C_{20}$ fluoro(oxy)hydrocarbon group, $C_1$-$C_{20}$ perfluoro(oxy)hydrocarbon group. Preferably $R_F$ is a $C_1$-$C_{20}$ perfluoro(oxy)hydrocarbon group. Non-limiting examples of suitable acyl halides of formula (IIa) are for instance: $CF_3COF$, $CF_3CF_2COF$, $CF_3CF_2CF_2OCF(CF_3)COF$, $(CF_3)_2CF$-$COF$, $ClCF_2COF$, $CF_3CF_2OCF_2COF$, $FC(O)CF_2[O(CF_2O)_n(CF_2CF_2O)_m]_pCF_2Q$, wherein m/n=0.5-10; p=0-20; Q=$CF_3$, H.

When the alcohol is represented by the formula $R_1R_2CHOH$ (I), wherein $R_1$ and $R_2$ have the above defined meanings, the reaction can be schematized as follows:

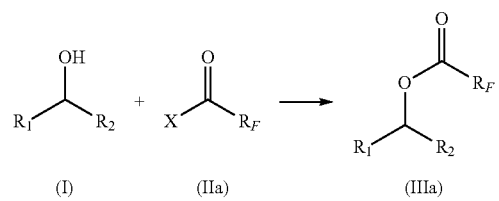

In an alternative embodiment of the process the at least partially hydrogenated alcohol (I) is converted into an at least partially hydrogenated diester compound by reaction with a diacyl halide of formula $XOCR_F'COX$ (IIb). In formula (IIb) X may be selected from F, Cl, Br; preferably X is F.

Group $R_F'$ in the diacyl halide of formula (IIb) is typically selected in the group consisting of divalent $C_1$-$C_{20}$ (oxy)

hydrocarbon group, divalent $C_1$-$C_{20}$ fluoro(oxy)hydrocarbon group, divalent $C_1$-$C_{20}$ perfluoro(oxy)hydrocarbon group. Preferably $R_F'$ is perfluorinated. Non-limiting examples of suitable diacyl halides of formula (IIb) are for instance: FOC—COF, FOCCF$_2$CF$_2$COF, FOCCF$_2$OCF$_2$COF, FC(O) CF$_2$ [O(CF$_2$O)$_x$(CF$_2$CF$_2$O)$_y$]$_z$CF$_2$C(O)F wherein x/y=0.5-10; z=0-20.

The reaction may be schematized as follows:

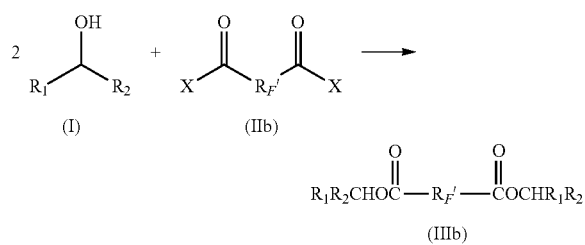

In step A of the process, the at least partially hydrogenated alcohol can be used pure, provided that it is liquid in the reaction conditions, or in a suitable diluent. Among suitable diluents, mention can be notably made of organic halogenated compounds, such as methylene chloride, CF$_3$OCFClCF$_2$Cl, perfluoropolyethers or hydrogen-containing fluoropolyethers (e.g. those commercialized under trade name GALDEN® PFPE or H-GALDEN® PFPE by Solvay Solexis S.p.A.), fluorinated or perfluorinated ethers (e.g. those commercialized under trade name NOVEC® fluids and HFE® ethers from 3M).

In step B of the process, the ester compound (IIIa) or (IIIb) resulting from step A is reacted with fluorine in the presence of a (per)haloolefin, as above defined, to obtain a perfluorinated ester compound.

According to one embodiment, the reaction can be schematized as follows:

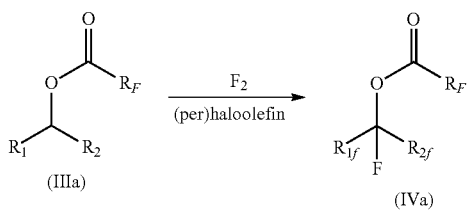

wherein $R_1$, $R_2$ are as above defined, $R_{1f}$ is the perfluorinated equivalent of $R_1$ and $R_{2f}$ is the perfluorinated equivalent of $R_2$. It is understood that if $R_1$ and/or $R_2$ is H, $R_{1f}$ and/or $R_{2f}$ is F; if $R_1$ or $R_2$ is perfluorinated, then $R_1$=$R_{1f}$ or $R_2$=$R_{2f}$, respectively.

According to one embodiment of the process, (per)haloolefins suitable for use in step B are those represented by the following formula:

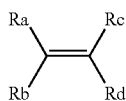

wherein $R_a$, $R_b$, $R_c$ and $R_d$ are each independently selected from the group consisting of F, Cl and hydrocarbon groups, possibly comprising one or more chlorine and/or fluorine atoms, optionally having one or more heteroatoms different from F and Cl, e.g. oxygen, possibly directly linked to the double bond. At least one of $R_a$, $R_b$, $R_c$ and $R_d$ is selected from fluorine or chlorine.

Preferably, $R_a$, $R_b$, $R_c$ and $R_d$ are each independently selected in the group consisting of F, Cl, $C_1$-$C_4$ perfluorocarbon groups, $C_1$-$C_4$ oxygen-containing perfluorocarbon groups, $C_1$-$C_4$ fluorochlorohydrocarbon groups, and $C_1$-$C_4$ oxygen-containing fluorochlorohydrocarbon groups. Still preferably, $R_a$, $R_b$, $R_c$ and $R_d$ are each independently selected in the group consisting of F, Cl, $C_1$-$C_2$ perfluorocarbon groups, $C_1$-$C_2$ oxygen-containing perfluorocarbon groups, $C_1$-$C_2$ fluorochlorohydrocarbon groups, and $C_1$-$C_2$ oxygen-containing fluorochlorohydrocarbon groups. Even more preferably at least three of $R_a$, $R_b$, $R_c$ and $R_d$ are selected from F, Cl.

As examples of such (per)haloolefins, mention may be made of $C_2$-$C_{18}$ fluoro and/or perfluoroolefins, preferably $C_2$-$C_{10}$ fluoro and/or perfluoroolefins, such as tetrafluoroethylene (TFE), hexafluoropropylene (HFP) and its dimers and trimers, octafluorobutene, perfluoropentene, perfluorohexene, perfluoroheptene, perfluorooctene, perfluorocyclobutene, perfluorocyclopentene, perfluorocyclohexene, chlorotrifluoroethylene, dichlorodifluoroethylene, chloropentafluoropropene, perfluorobutadiene, perfluoromethylvinylether, perfluoroethylvinylether, perfluoropropylvinylether; CF$_3$OCCl=CClF, trichloroethylene, tetrachloroethylene, dichloroethylene isomers; and fluorodioxoles of formula:

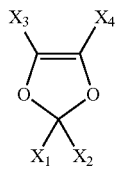

wherein $X_1$, $X_2$, $X_3$, and $X_4$, equal to or different from each other, are independently selected from F, $R_f$ and $OR_f$, wherein $R_f$ is a (per)fluorocarbon group, and wherein at least one of $X_3$, and $X_4$ is fluorine. Preferably the (per)haloolefin is selected from the group consisting of tetrafluoroethylene (TFE), hexafluoropropylene (HFP) and its dimers and trimers, more preferably from the group consisting of tetrafluoroethylene (TFE) and hexafluoropropylene (HFP).

The amount of (per)haloolefin used in step B of the process is not critical. According to one embodiment, the amount of said (per)haloolefin is comprised in the range of 0.1 to 30 mol % with respect to the hydrogen atoms contained in the ester compound. Preferably, said amount is comprised in the range of 0.5 to 20 mol % with respect to the hydrogen atoms contained in the ester compound. More preferably, said amount is comprised in the range of 1 to 15 mol % with respect to the hydrogen atoms contained in the ester compound.

The (per)haloolefin can be initially loaded in the reaction vessel or can be advantageously continuously fed in the required amount during the fluorination reaction.

Fluorine may be fed into the reactor as a pure gas or diluted with an inert gas, such as $N_2$, Ar and He.

A hydrogen fluoride scavenger may be used (e.g. NaF, KF).

The ester compound may be allowed to react with fluorine in a non-solvent phase, provided that it is liquid in the reaction conditions, as well as diluted in a suitable solvent.

Surprisingly, the use of concentrated or pure reagents in step B of the process does not lead to decomposition of the reagents, as the reaction exothermicity may be controlled.

As a matter of fact, the reaction temperature may be advantageously maintained in the range of −100° C. to +50° C.

Typically, fluorine and the (per)haloolefin, in separate feeds, are continuously added to the ester at the given temperature of the process. Generally fluorine is added to the reaction in an amount slightly higher than the stoichiometric amount necessary to convert all the hydrogen atoms in the ester to fluorine atoms. Typically, the amount of net fluorine added to the reaction is roughly 30 mol %, preferably 20 mol %, more preferably 10 mol % higher than said stoichiometric amount. The expression "net fluorine" indicates the amount of fluorine that has not been consumed in the reaction with the (per)haloolefin to give a perfluorohaloalkane. The net fluorine corresponds to the total amount of fed fluorine minus the amount that reacts stoichiometrically with the (per)haloolefin.

Advantageously, no temperature increase is required to perform the complete fluorination of the ester (IIIa) or (IIIb).

The end of the reaction can be advantageously detected by online analysis, by checking fluorine conversion, which typically suddenly drops to zero.

According to a further embodiment of the process, a further step is comprised, namely:

C. cleaving said perfluorinated ester compound.

The skilled person will readily understand that, if a primary alcohol is used as the starting at least partially hydrogenated alcohol then cleaving step C leads to a perfluorinated acyl fluoride. Under the same conditions, if a secondary alcohol is used as the starting at least partially hydrogenated alcohol then cleaving step C yields a perfluorinated ketone.

According to an embodiment of the process, step C may be schematized as follows:

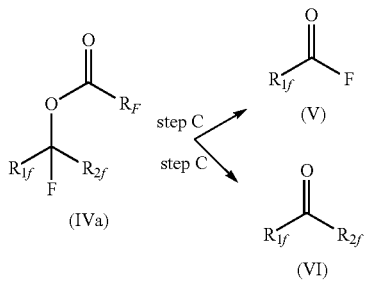

wherein $R_{1f}$ and $R_{2f}$ have the meanings given above. As above mentioned, although the same reaction conditions of step C are applied, a perfluorinated acyl fluoride (V) results as product of this step if at least one of groups $R_{1f}$ or $R_{2f}$ is F. For illustration purpose only, in the above scheme the situation where $R_{2f}$ is F is shown. In case that both groups $R_{1f}$ or $R_{2f}$ are other than F, step C yields a ketone (VI).

Any suitable cleaving or decomposition method or reaction may be used in step C of the process. Said cleaving reaction may be accomplished by thermolysis in the presence of metal fluorides, such as NaF, CaF₂, BaF₂, AgF, CsF, KF. The temperature for the thermolysis reaction of step C may be comprised in the range of −70° C. to 220° C.; preferably, the temperature may be comprised in the range of −30° C. to 150° C.

The invention will be now described in more detail with reference to the following examples, whose purpose is merely illustrative and not intended to limit the scope of the invention. Should the disclosure of any patents, patent applications, and publications which are incorporated herein by reference conflict with the description of the present application to the extent that it may render a term unclear, the present description shall take precedence.

EXAMPLES

Example 1

Conversion of Alcohol in Fluoroester

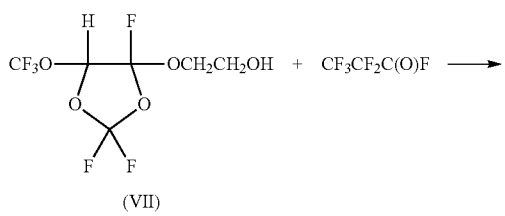

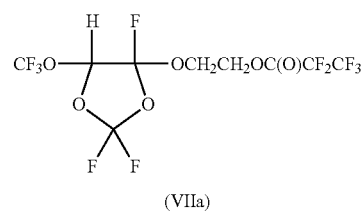

In a 250 ml stainless steel reactor equipped with mechanic stirrer, gas inlet, gas outlet, a thermocouple to check the internal temperature and external cooling bath, 120 g of the alcohol of formula (VII) and 27.8 g of powdered NaF were introduced and the external temperature set at −5° C. Then, 3.0 Nl/h of CF₃CF₂C(O)F diluted with 1.0 Nl/h of N₂ were introduced into the reactor under vigorous stirring. The off-gases were analysed to evaluate CF₃CF₂C(O)F conversion. After 3.5 hours CF₃CF₂C(O)F feeding was stopped and excess CF₃CF₂C(O)F removed by nitrogen flow. The crude mixture was filtered to separate the inorganic salts. The liquid product was analyzed by ¹⁹F NMR showing an almost quantitative conversion of the starting alcohol and selectivity in the desired fluoroester.

Example 2

Perfluorination of Fluoroester of Formula (VIIa)

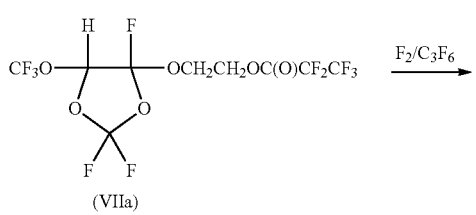

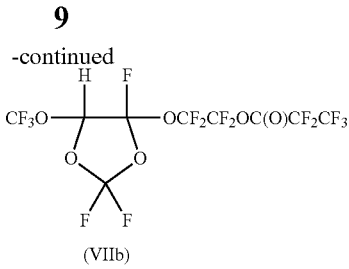

(VIIb)

In a 250 ml stainless steel reactor equipped with mechanic stirrer, two gas inlets, one gas outlet, a thermocouple to check the internal temperature and external cooling bath, 49 g of the fluoroester (VIIa) were loaded in the reactor and the external temperature set at 0° C.

Then, two different streams of gases were introduced by the inlets into the reactor kept under vigorous stirring: $F_2$ (1.6 Nl/h) diluted with 3.0 Nl/h of He, and $C_3F_6$ (0.1 Nl/h) diluted with 1.5 Nl/h of He. The off-gases passed through NaF to trap the HF formed and were analyzed by GC to evaluate fluorine conversion and thus estimate the C—H to C—F conversion. The internal temperature remained constant during the reaction at +5° C. After 10.3 hours, the internal temperature dropped quickly from 5° C. to 0° C., and no additional $F_2$ conversion was observed. The feeding of the gases was stopped and the residual HF was removed by inert gas. The crude mixture was collected and analyzed by $^{19}$F-NMR. The perfluoroester (VIIb) was obtained with quantitative conversion and 92% selectivity.

Example 3

Conversion of 1-propanol in Propylperfluoropropionate

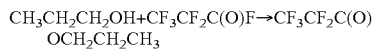

In a 150 ml stainless steel reactor equipped with magnetic stirrer and pressure gauge, 30.2 g of 1-propanol and 29.4 g of powdered NaF were loaded; perfluoropropionyl fluoride (contained in a cylinder equipped with a pressure reducer set at 3 bar) was allowed to flow into the reactor at room temperature.

When all 1-propanol reacted the excess propionyl fluoride was vented away and the crude mixture was filtered to separate the inorganic salts. The liquid product was analyzed by $^{19}$F-NMR showing an almost quantitative conversion of the starting alcohol and selectivity in the desired propylperfluoropropionate.

Example 4

Perfluorination of Propylperfluoropropionate

In the same apparatus of Example 2, 10 g of propylperfluoropropionate diluted in 50 g of $CF_3OCFClCF_2Cl$ were introduced and fluorinated at −30° C. as in Example 2. After 5 hours and 40 minutes, the internal temperature fell quickly from −25° C. to −30° C., and no additional $F_2$ conversion was observed. The crude mixture was collected and analyzed by $^{19}$F-NMR. The desired perfluoropropylpropionate was obtained with quantitative conversion and 94% selectivity.

Example 5

Esterification of Diethylen Glycol with Perfluoropropionyl Fluoride

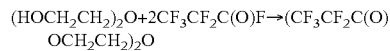

The same procedure described in Example 3 was repeated using a 300 ml stainless steel reactor, 53 g of diethylen glycol and 50 g of powdered NaF. The liquid product after filtration was analyzed by $^{19}$F-NMR showing an almost quantitative conversion of the starting alcohol and selectivity in the desired ester.

Example 6

Perfluorination of the Ester $(CF_3CF_2C(O)OCH_2CH_2)_2O$

In the same apparatus of Example 2, 12 g of $(CF_3CF_2C(O)OCH_2CH_2)_2O$ diluted in 50 g of $CF_3OCFClCF_2Cl$ were introduced and fluorinated at −30° C. as in Example 2. After 4 hours, the internal temperature fell quickly from −25° C. to −30° C., and no additional $F_2$ conversion was observed. The crude mixture was collected and analyzed by $^{19}$F-NMR. $(CF_3CF_2C(O)OCF2CF_2)_2O$ was obtained with quantitative conversion and an 85% selectivity.

Example 7

Esterification of 1-propanol with a Diacyl Fluoride

In a stainless steel 150 ml reactor equipped with mechanical stirrer 90 g of a perfluoropolyether (PFPE) diacyl fluoride having general formula $FC(O)CF_2O(CF_2O)_h(CF_2CF_2O)_gCF_2C(O)F$ wherein h and g are such that the average equivalent weight is 285 g/mol, were introduced, the reactor was cooled at 0° C. and 19 g of 1-propanol were added under vigorous stirring in one hour. The HF formed was vented away introducing nitrogen gas in the reactor while increasing the internal temperature to 25° C. IR, $^{19}$F-NMR and $^{1}$H-NMR analyses confirmed the quantitative conversion of the diacyl fluoride and the formation of the corresponding ester (102 g of PFPE diester).

Example 8

Perfluorination of $CH_3CH_2CH_2OC(O)$—PFPE-$C(O)OCH_2CH_2CH_3$

The crude mixture from Example 7 was cooled at −30° C. and fluorinated in the same reactor as described in Example 2 feeding 3.0 Nl/h of fluorine (He/$F_2$=2/1) together with 0.3 Nl/h of $C_3F_6$ (He/$C_3F_6$=5/1). After 20 hours the internal temperature fell quickly from −23° C. to −30° C., and no additional $F_2$ conversion was observed. The crude mixture was collected and analyzed by $^{19}$F NMR. The desired perfluoroester CF$_3$CF$_2$CF$_2$OC(O)—PFPE-C(O)OCF$_2$CF$_2$CF$_3$ was obtained with quantitative conversion and 91% selectivity.

Example 9

Cleavage of CF$_3$CF$_2$CF$_2$OC(O)—PFPE-C(O)OCF$_2$CF$_2$CF$_3$ to CF$_3$CF$_2$COF In a 100 ml glass reactor equipped with magnetic stirrer and a reflux condenser maintained at 20° C. and connected to a trap cooled at −75° C., 80 g of the perfluorodiester of Example 8 and 1 g of anhydrous KF were heated at 70° C. for 5 hours under vigorous stirring. A liquid sample (25.4 g) was recovered in the cold trap. The product was identified by GC and NMR analysis as CF$_3$CF$_2$COF at 99% purity (94% yield).

Possible modifications and/or additions may be made by those skilled in the art to the hereinabove disclosed and illustrated embodiment while remaining within the scope of the following claims.

The invention claimed is:

1. A process for producing a perfluorinated functional compound, the process comprising:
   A) converting an at least partially hydrogenated alcohol into a corresponding at least partially hydrogenated ester compound; and
   B) reacting said at least partially hydrogenated ester compound with fluorine in the presence of at least one (per)haloolefin comprising at least one carbon-carbon double bond and having at least one fluorine or chlorine atom on either one of the carbon atoms of said double bond, to obtain a perfluorinated ester compound.

2. The process according to claim 1, wherein said at least partially hydrogenated alcohol complies with formula R$_1$R$_2$CHOH, wherein R$_1$ and R$_2$, independently of each other, are selected from the group consisting of H, straight-chain, branched-chain and cyclic (oxy)hydrocarbon group, straight-chain, branched-chain and cyclic fluoro(oxy)hydrocarbon group and wherein R$_1$ and R$_2$, independently of each other, may optionally comprise one or more —OH groups.

3. The process according to claim 2, wherein R$_1$ and R$_2$, equal to or different from each other, are independently selected from the group consisting of H, C$_1$-C$_{20}$ (oxy)hydrocarbon group, C$_1$-C$_{20}$ fluoro(oxy)hydrocarbon group, C$_3$-C$_{20}$ cyclo(oxy)hydrocarbon group, and C$_3$-C$_{20}$ fluorocyclo(oxy)hydrocarbon group.

4. The process according to claim 1, wherein said at least partially hydrogenated alcohol is reacted with an acyl halide of formula R$_F$COX, wherein R$_F$ is selected from the group consisting of C$_1$-C$_{20}$ (oxy)hydrocarbon group, C$_1$-C$_{20}$ fluoro(oxy)hydrocarbon group, and C$_1$-C$_{20}$ perfluoro(oxy)hydrocarbon group, and wherein X=F, Cl, Br.

5. The process according to claim 1, wherein said at least partially hydrogenated alcohol is reacted with a diacyl halide of formula XOC—R$_F$'—COX wherein R$_F$' is selected from the group consisting of divalent C$_1$-C$_{20}$ (oxy)hydrocarbon group, divalent C$_1$-C$_{20}$ fluoro(oxy)hydrocarbon group, and divalent C$_1$-C$_{20}$ perfluoro(oxy)hydrocarbon group, and wherein X=F, Cl, Br.

6. The process according to claim 1, wherein said (per)haloolefin complies with the following formula:

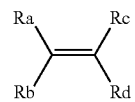

wherein R$_a$, R$_b$, R$_c$ and R$_d$ are each independently selected in the group consisting of F, Cl and hydrocarbon groups, wherein the hydrocarbon group optionally comprises one or more chlorine and/or fluorine atoms, and wherein the hydrocarbon group optionally includes one or more heteroatoms different from fluorine and chlorine, optionally directly linked to the double bond.

7. The process according to claim 6, wherein R$_a$, R$_b$, R$_c$ and R$_d$ are each independently selected from the group consisting of F, Cl, C$_1$-C$_4$ perfluorocarbon groups, C$_1$-C$_4$ oxygen-containing perfluorocarbon groups, C$_1$-C$_4$ fluorochlorohydrocarbon groups, and C$_1$-C$_4$ oxygen-containing fluorochlorohydrocarbon groups.

8. The process according to claim 1, wherein said (per)haloolefin is selected from the group consisting of: tetrafluoroethylene (TFE), hexafluoropropylene (HFP) and its dimers and trimers, octafluorobutene, perfluoropentene, perfluorohexene, perfluoroheptene, perfluorooctene, perfluorocyclobutene, perfluorocyclopentene, perfluorocyclohexene, chlorotrifluoroethylene, dichlorodifluoroethylene, chloropentafluoropropene, perfluorobutadiene, perfluoromethylvinylether, perfluoroethylvinylether, perfluoropropylvinylether; CF$_3$OCCl=CClF, trichloroethylene, tetrachloroethylene; and fluorodioxoles of formula:

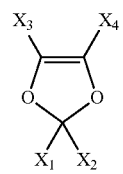

wherein X$_1$, X$_2$, X$_3$, and X$_4$, equal to or different from each other, are independently selected from F, R$_f$ and OR$_f$, wherein R$_f$ is a (per)fluorocarbon group.

9. The process according to claim 1, wherein the amount of said (per)haloolefin is in the range of 0.1 to 30% moles with respect to said at least partially hydrogenated ester.

10. The process according to claim 1, further comprising cleaving said perfluorinated ester compound.

11. The process according to claim 10, wherein cleaving of said perfluorinated ester compound is achieved by thermolysis in the presence of a metal fluoride.

* * * * *